United States Patent [19]
Hahn

[11] Patent Number: 5,709,823
[45] Date of Patent: Jan. 20, 1998

[54] METHOD FOR PRODUCING SONOTRODES

[75] Inventor: Rainer Hahn, Rottenburg, Germany

[73] Assignee: THERA patent Gmbh & Co. KG Gesellschaft für industrielle Schutzrechte, Seefeld, Germany

[21] Appl. No.: 714,365

[22] Filed: Sep. 16, 1996

Related U.S. Application Data

[62] Division of Ser. No. 164,554, Dec. 10, 1993, abandoned.

[30] Foreign Application Priority Data

Dec. 12, 1992 [DE] Germany .................. 42 41 936.0

[51] Int. Cl.$^6$ .................. A61C 13/00; A61C 13/20; A61C 13/08
[52] U.S. Cl. .................. 264/16; 264/17; 264/19; 264/430; 264/443
[58] Field of Search .................. 264/16, 17, 19, 264/430, 442, 443

[56] References Cited

U.S. PATENT DOCUMENTS

| | | | |
|---|---|---|---|
| 3,222,443 | 12/1965 | Dames, Jr. et al. | 264/225 |
| 3,971,133 | 7/1976 | Mushabac | 32/2 |
| 4,710,334 | 12/1987 | Rossetti . | |

FOREIGN PATENT DOCUMENTS

| | | |
|---|---|---|
| 36 06 304 A1 | 9/1986 | Germany . |
| 36 17 790 A1 | 1/1987 | Germany . |
| 39 28 684 C2 | 10/1991 | Germany . |

*Primary Examiner*—Christopher A. Fiorilla
*Attorney, Agent, or Firm*—Foley & Lardner

[57] ABSTRACT

A dental restoration part is produced from a ceramic material by a method of ultrasonic working. The method includes forming a negative mold from a master sonotrode, forming a pre-working sonotrode from the negative mold, and ultrasonically working a workpiece using the pre-working sonotrode. The master sonotrode is then used to ultrasonically work the workpiece to form the dental restoration part.

11 Claims, 2 Drawing Sheets

METHOD FOR PRODUCING SONOTRODES

This application is a division of application Ser. No. 08/164,554, filed Dec. 10, 1993, now abandoned.

BACKGROUND OF THE INVENTION

A method of producing sonotrodes for ultrasonic working of ceramic workpieces for dentures.

The invention deals with the ultrasonic working of workpieces for producing structural parts and, in particular, ceramic dentures such as, for instance, dental veneers, inlays, crowns or bridges made from ceramic workpieces, i.e. more particularly, high-performance ceramics and monocrystals as well as the production of tools being suited therefor.

More specifically, the invention relates to a method or an apparatus respectively.

Such methods and apparatus have been described in DE 3 928 684 C2 (Hahn) and in German patent application P 42 32 023.2-35 (Hahn).

Moreover, P 42 32 023.2-35 describes a method and an apparatus for producing presonotrodes, for instance by fixing a plastic presonotrode crown on a prefabricated secondary sonotrode, and a geometrical model of an ultrasonic working machine. Reference is expressly made to this patent application as well as to the prior art cited therein in order to avoid reiterations and the entire disclosure thereof is made supplementary subject-matter of the present patent application.

SUMMARY OF THE INVENTION

The invention deals with the problem of the economic production of tooth restoration from ceramics, for instance, by means of ultrasonic working.

The subject-matters according to the invention make it possible to clearly accelerate the manufacturing process and simultaneously to improve form-fitting, the mechanical characteristics and the surface parameters of the machined workpiece by first machining the workpiece with a pre-working sonotrode and subsequently finishing it with the original sonotrode.

Thus, the subject-matters of the claims describe copies of the original sonotrodes and the spatial relation thereof to the longitudinal machining axis. It is thereby possible to carry out the ultrasonic working of one or both surface halves of the workpiece to be manufactured in two (respectively) consecutive work steps.

First the pre-working sonotrode is hobbed into the workpiece up to short of the desired hobbing depth, e.g. using the ultrasonic working machine described in P 42 32 023.2-35. A coarse slurry, higher amplitudes, higher power and higher contact pressures may be used for first elaborating from the workpiece a coarse mould as the negative of the pre-working sonotrode, which clearly results in an accelerated process.

In a subsequent working step, the finishing step, the pre-working sonotrode is removed from the ultrasonic working machine, the original sonotrode is introduced and applied in form-fitting engagement with the workpiece, which has already been pre-machined, or the workpiece is aligned in relation to the original sonotrode and subsequently machined up to the desired hobbing depth. In this working cycle, "dampened" process magnitudes such as, for instance, fine-grained slurry, low amplitudes and contact pressures are particularly suitable for obtaining optimum surface conditions. Moreover, wear on the sonotrode surface may thereby be reduced, which results in an improved accuracy being achieved.

In order to increase resistance to wear, the original sonotrodes and/or the pre-working sonotrodes or, at least, the sonotrode crowns thereof are preferably reshaped in metal. For the purpose, the original sonotrode, for instance, and/or the pre-working sonotrode is metal-cast according to the principle of the lost mould.

In order to further optimize wear behaviour, the surface of the original sonotrode crown and/or the pre-working sonotrode crown or, respectively, its metal equivalents mentioned above may be defined, e.g. thermally aftertreated and/or infiltrated with suitable substances, e.g. cobalt, chromium or silicon and/or may be coated in thin-film technique.

DESCRIPTION OF THE DRAWINGS

In the following, the invention will be described in detail from embodiments and upon reference to the annexed drawings.

DESCRIPTION OF THE PREFERRED EMBODIMENT

The manufacture of originals of sonotrodes or merely of sonotrode crowns is basically carried out in the manner described in P 42 32 023.2-35. The sonotrodes or sonotrode crowns manufactured accordingly serve as models for the manufacture of pre-working sonotrodes or the crowns thereof (as described in the following) and serve, in a subsequent finishing step equally described below, as finishing sonotrodes for ultrasonic working of a workpiece.

Figure 1:
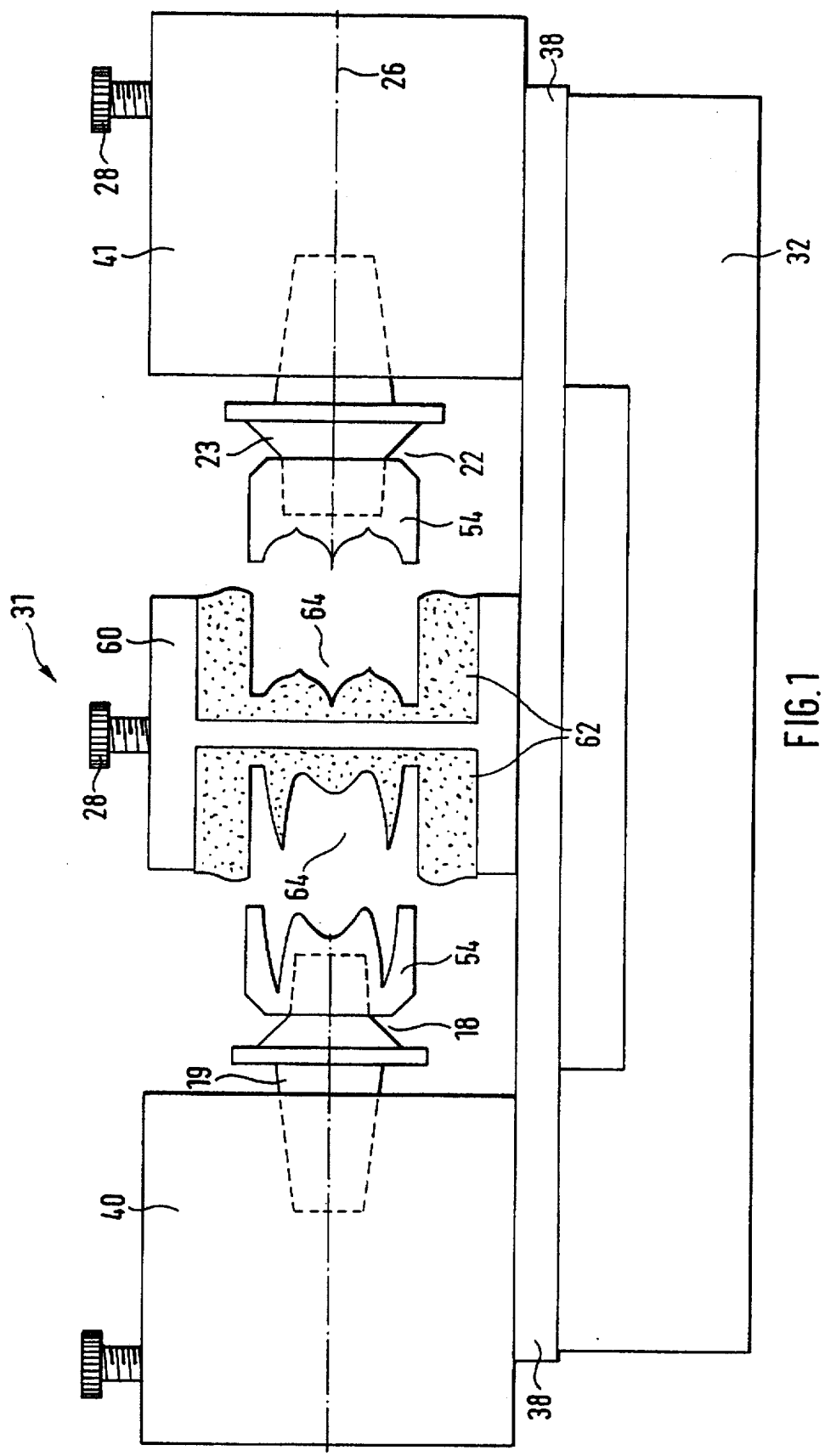
FIG. 1 is a schematical view of an apparatus at an initial phase of the method of the invention.

The moulding of the original sonotrode crowns is represented in FIG. 1: the invention is based upon the moulding of one or both original sonotrode crowns 54 of a sonotrode 18, 22 by means of a suitable doubling part 60 having recesses formed on the side facing sonotrode crown 54 or on both sides thereof for receiving a plastic or curable substance such as a precision plastic moulding or doubling substance 62. The doubling part 60 may be formed in any manner and be mounted in a reproducible manner in the guide rail(s) 38 of an alignment device and may be fixed with the aid of a tensioning bracket 28 or magnetically, for instance. The use of apparatus 31, which may for instance consist of a base plate 32, guide rails 38 and sonotrode receiving members 40, 41 is known as regards the manufacture of sonotrodes 18, 22 as described in P 42 32 023.2-35 and facilitates spatial allocation of original sonotrode crowns 54, negative moulds 64, sonotrode bodies 19, 23 and plastic substance 62, for instance.

The original sonotrode crowns 54 of a sonotrode 18, 22 are preferably fixed individually, successively in time or simultaneously in sonotrode receiving members 40, 41 of aligning device 31 and moved towards each other by relatively moving sonotrode receiving members 40, 41 towards each other and doubling part 60 filled with plastic moulding substance 62 in parallel to the virtual longitudinal machining axis 26 on one side or on both sides until original sonotrode crowns 54 are completely enclosed by doubling or moulding substance 62. In order to achieve accurate moulding, precision moulding substances such as, for instance, addition cross-linked silicones or polyether are preferably used.

After curing of moulding substance 62, original sonotrode crowns 54 or sonotrodes 18, 22, respectively, are removed from negative mould 64 and sonotrode receiving members 40, 41 individually, successively in time or simultaneously and one or two formally equivalent sonotrode bodies 19, 23 are fixed in corresponding sonotrode receiving members 40, 41.

Figure 2:
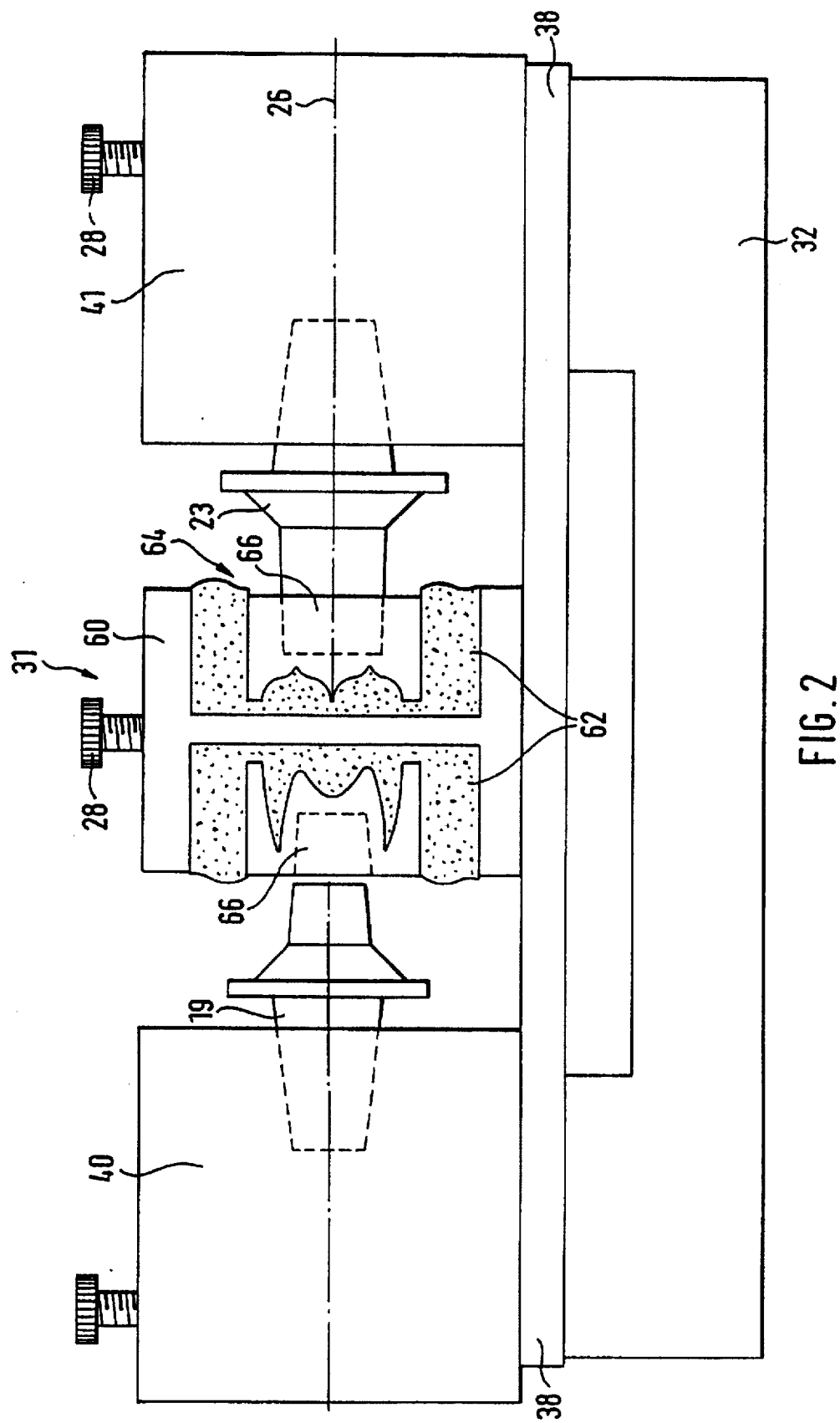
FIG. 2 is a schematical view of the apparatus of FIG. 1 at a later phase of the method.

As is represented in FIG. 2, negative moulds 64 are then filled individually, successively in time or simultaneously, outside or inside the apparatus with a plastically processable and subsequently curing or curable substance 66 such as, for instance, a plastic material or wax and sonotrode bodies 19, 23 are brought, individually, successively in time or simultaneously, into direct form-fitting engagement with plastic substance 66 in doubling part 60 repositioned in guide rails 38 of apparatus 31 and fixed in parallel to the longitudinal machining axis 26 until plastic substance 66 has been cured. If it is provided to transfer the sonotrodes into metal by casting, a plastic material or a wax is usefully chosen which burns without leaving any residue. Subsequently, the copies of original sontrodes 18, 22 may be removed from the apparatus. For easier allocation of original sonotrodes 18, 22 and the workpiece during ultrasonic working, original sonotrode crowns 54 are preferably provided with a marking such as a small notch or a boss, for instance, at the largest diameter of their outer surface before the moulding thereof and their outer periphery is slightly reduced (ground) after moulding.

Of course, the basic inventive idea may also be implemented by moulding the original sonotrodes already transferred into metal or the crowns thereof.

However, it is advisable in carrying out the casting method, to embed the original sonotrodes together with the pre-machining sonotrodes in a refractory mould and to cast sonotrodes 54, 66 in metal onto sonotrode bodies 19, 23 in order to avoid relative casting inaccuracies in various casting processes. Adhesion between the sonotrode body and the sonotrode crown may for instance be improved by additional bonding or a soldering or welding joint.

For producing the ceramic structural part proper, which is a ceramic part in particular, the pre-working sonotrode produced in accordance with the method according to the invention is first inserted in the ultrasonic working machine described in P 42 32 023.2-35 in a first working step, it is connected with the ultrasonic transducer and hobbed into the workpiece up to short of the desired hobbing depth via ultrasonic energy. The process magnitudes are selected in view of optimum time span volumes. Operation is preferably effected at high power take-up, high contact pressure and amplitude as well as a coarse-grained hard grain suspension such as an aqueous diamond or boron carbide suspension.

In a subsequent second working step, the pre-working sonotrode is removed from the ultrasonic working machine and replaced with the corresponding original sonotrode. Relative alignment of the pre-worked workpiece is achieved through the dimensional congruence of the sonotrode crown and is facilitated by the above-mentioned markings as well as the reduction of the outer periphery of the original sonotrode.

After the spatial relationship between the pre-worked workpiece and the original sonotrode has been fixed, final machining of the workpiece up to the desired hobbing depth is carried out. The process magnitudes of ultrasonic working are preferably adapted to this "finishing step", for instance by preselecting lower contact pressures, lower amplitudes and reduced power take-up.

I claim:

1. A method of producing a dental restoration part from a ceramic material by means of ultrasonic working, comprising:

(a) forming a negative mold from a master sonotrode, (b) forming a pre-working sonotrode from said negative mold, (c) ultrasonically working a workpiece using said pre-working sonotrode, and (d) ultrasonically working said workpiece made of ceramic material using said master sonotrode to form said dental restoration part.

2. A method according to claim 1, wherein step (a) includes moving said master sonotrode and a doubling part provided with a molding substance relatively toward each other and curing said molding substance, thereby forming a hollow mold as said negative mold, and step (b) includes filling said hollow mold with a plastic substance and engaging said plastic substance in form-fitting manner with a sonotrode body from an open side of said negative mold, thereby forming said pre-working sonotrode comprising said sonotrode body and said plastic substance.

3. A method according to claims 2, wherein, in step (a), said master sonotrode and said molding substance are moved relatively to each other along a designated, working axis defined by said master sonotrode.

4. A method according to claim 3, wherein step (a) comprises the following sub-steps:

locking said master sonotrode in a sonotrode receiving member;

moving said master sonotrode toward said doubling part filled with said molding substance along said working axis;

separating said master sonotrode from said molding substance after said molding substance has cured, removing said master sonotrode from said receiving member and locking said sonotrode body in said receiving member, and moving said sonotrode body toward said doubling part so as to penetrate into said plastic material.

5. A method according to claim 2, wherein a double-sided doubling part is used and molding substance is provided on both sides thereof to permit the simultaneous production of a pair of pre-working sonotrodes from a corresponding pair of master sonotrodes.

6. A method according to claim 1, wherein, after step (a), master sonotrode is reduced in size by grinding an outer diameter portion thereof.

7. A method according to claim 1, wherein a crown portion of said master sonotrode is hardened.

8. A method according to claim 1, wherein a crown portion of said master sonotrode is made of metal.

9. A method according to claim 1, wherein a crown portion of said pre-working sonotrode is hardened.

10. A method according to claim 1, wherein a crown portion of said pre-working sonotrode is made of metal.

11. A method according to claim 1, wherein said dental restoration part is a dental veneer, an inlay, a crown or a bridge.

* * * * *